(12) United States Patent
Sauzeat

(10) Patent No.: US 6,927,235 B2
(45) Date of Patent: Aug. 9, 2005

(54) VACCINE COMPOSITION COMPRISING IRON PHOSPHATE AS VACCINE ADJUVANT

(75) Inventor: Elisabeth Sauzeat, Lentilly (FR)

(73) Assignee: Sanofi Pasteur S.A., Lyons Cedex (FR)

( * ) Notice: Subject to any disclaimer, the term of this patent is extended or adjusted under 35 U.S.C. 154(b) by 0 days.

(21) Appl. No.: 10/845,883

(22) Filed: May 14, 2004

(65) Prior Publication Data

US 2004/0228880 A1 Nov. 18, 2004

Related U.S. Application Data

(60) Provisional application No. 60/479,042, filed on Jun. 16, 2003.

(30) Foreign Application Priority Data

May 16, 2003 (FR) .............................. 03 05876

(51) Int. Cl.[7] .............................................. A01N 55/02
(52) U.S. Cl. ............................ 514/502; 514/2; 514/75; 424/278.1; 424/284.1; 424/216.1; 424/245.1; 424/247.1
(58) Field of Search .............................. 514/2, 75, 502; 424/278.1, 216.1, 284.1, 245.1, 247.1

(56) References Cited

U.S. PATENT DOCUMENTS 5,895,653 A * 4/1999 Eibl et al. ................ 424/204.1

OTHER PUBLICATIONS

Elixir.com webpage for Product: Ferrum Phosphate 6X 500 tablets.*

A. J. Parsons et al. "Synthesis and degradation of sodium iron phosphate glasses and their in vitro cell response", Journal of Biomedical Materials Research Part A, vol. 71A, Issue 2, pp. 283–291, Published Online: Aug. 24, 2004.*

* cited by examiner

*Primary Examiner*—Jeffrey Stucker
(74) *Attorney, Agent, or Firm*—McDonnell Boehnen Hulbert & Berghoff LLP

(57) ABSTRACT

The present invention relates to vaccine compositions comprising iron phosphate as adjuvant. This iron phosphate is in the form of particles, the size of which is between 0.01 $\mu$m and 300 $\mu$m; it can be obtained by mixing a solution of iron salt and of phosphate salt.

8 Claims, 2 Drawing Sheets

VACCINE COMPOSITION COMPRISING IRON PHOSPHATE AS VACCINE ADJUVANT

This application claims the benefit of U.S. Provisional Application No. 60/479,042, filed Jun. 16, 2003.

The present invention relates to the vaccines field, and in particular to the field of vaccine compositions comprising an adjuvant. More particularly, the present invention relates to a vaccine in which the adjuvant comprises iron phosphate.

Vaccine compositions comprising adjuvants intended to increase or to qualitatively modify the immune response induced when an antigen is administered are known in the prior art. In fact, the developments realized in the vaccine industry result in the use of antigens obtained from viruses or from bacteria, but with increasingly developed purification methods, and also of antigens derived from biotechnology. These antigens have the advantage of generally being purer than some of the antigens used in the past, but, in return, they are often less immunogenic and therefore require the use of an adjuvant.

Many adjuvants have already been described: saponins, emulsions, cationic lipids, etc.

However, to date, the only adjuvants commonly used in the marketed products are aluminum-based adjuvants. Now, it would be desirable to have other adjuvants.

Among the prior art relating to adjuvants, mention may in particular be made of U.S. Pat. No. 5,895,653, which describes, as adjuvant, iron hydroxide compounds in the form of a colloidal solution, the adsorbent capacity of which is thought to be improved compared to the iron hydroxides previously described in the form of a gel.

However, such adjuvants, while they present an alternative to the aluminum-based adjuvants currently used, cannot always effectively replace them, and it is therefore desirable to have other compounds, the characteristics of which are such that at the same time they exhibit good tolerance with respect to the organisms to which they are administered, they can be produced under conditions compatible with the constraints of the pharmaceutical industry and, especially, they make it possible to increase or to modify the immune response to vaccine antigens in a manner which is at least as effective as the aluminum-based compounds currently used.

With this aim, the subject of the present invention is a vaccine composition comprising at least one vaccine antigen and at least one adjuvant, wherein the adjuvant comprises iron phosphate.

According to a particular characteristic, the iron phosphate is present in the form of a suspension of particles, the size of which is between 0.01 μm and 300 μm, and more particularly between 1 and 40 μm, with in particular a large proportion of particles, the size of which is approximately 7 μm.

According to a particular embodiment of the present invention, the iron phosphate is prepared from a solution of iron salt and of phosphate salt.

Such a preparation makes it possible to obtain a whitish non-crystalline product providing all the safety conditions required for administration to humans, generally in good health.

Many advantages of the present invention will emerge in the course of the description which will follow with reference to the figures which illustrate results obtained in the tests described in example 3;

FIG. 1 represents the IgG1 results after a 1st immunization, while

FIG. 2 represents the results obtained after the 2nd immunization;

FIG. 3 represents the IgG2a results obtained after the 1st immunization, while

FIG. 4 represents the results obtained after the 2nd immunization.

Figures 1, 2:
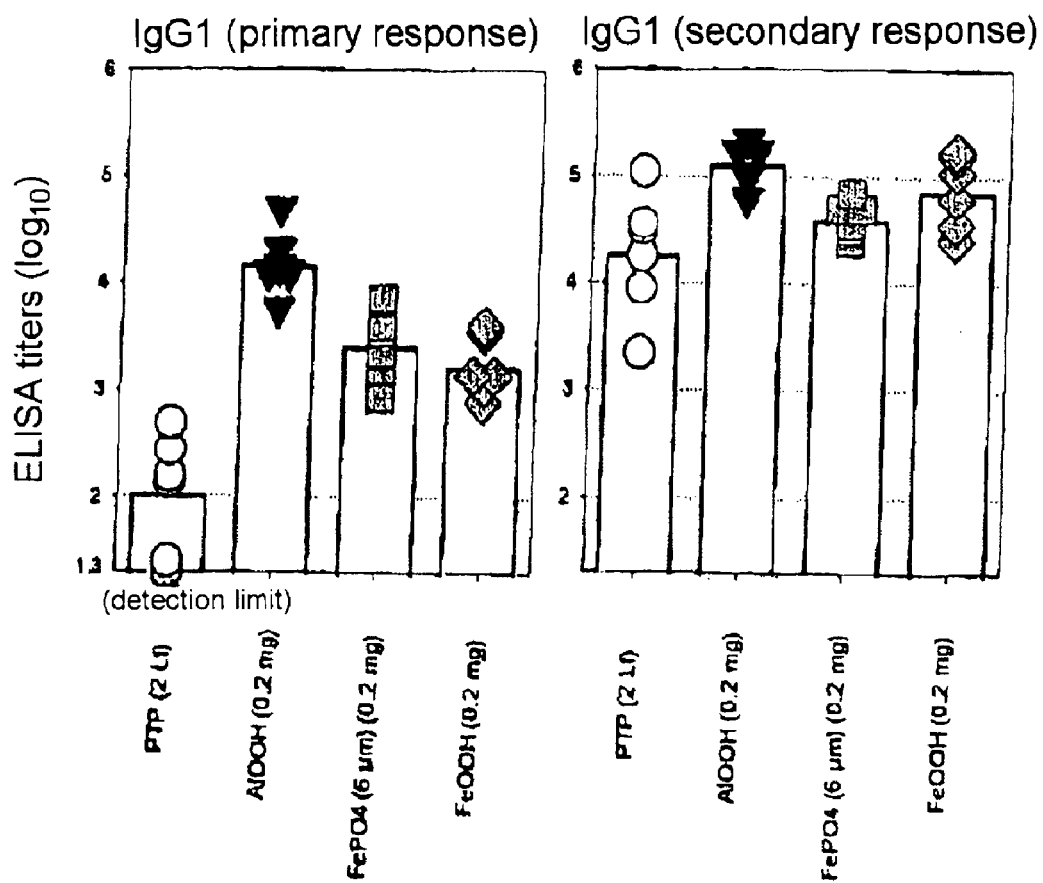

For the purpose of the present invention, the term "vaccine composition" is intended to mean a composition which can be administered to humans or to animals in order to induce an immune system response; this immune system response can result in a production of antibodies or simply in the activation of certain cells, in particular antigen-presenting cells, T lymphocytes and B lymphocytes. The vaccine composition can be a composition for prophylactic purposes or for therapeutic purposes, or both.

For the purpose of the present invention, the term "antigen" is intended to mean any antigen which can be used in a vaccine, whether it involves a whole microorganism or a subunit, and whatever its nature: peptide, protein, glycoprotein, polysaccharide, glycolipid, lipopeptide, etc. They may be viral antigens, bacterial antigens, or the like; the term "antigen" also comprises the polynucleotides, the sequences of which are chosen so as to encode the antigens whose expression by the individuals to which the polynucleotides are administered is desired, in the case of the immunization technique referred to as DNA immunization. They may also be a set of antigens, in particular in the case of a multivalent vaccine composition which comprises antigens capable of protecting against several diseases, and which is then generally referred to as a vaccine combination, or in the case of a composition which comprises several different antigens in order to protect against a single disease, as is the case for certain vaccines against whooping cough or the flu, for example.

Particularly good results have in particular been obtained with a vaccine composition comprising antigens against diphtheria, tetanus and poliomyelitis.

For the purposes of the present invention, the iron phosphate is an inert mineral compound based on amorphous, crystalline or pseudocrystalline iron phosphate. Very satisfactory tests have been achieved with an amorphous iron phosphate.

Such a compound is prepared from a solution of iron salt and of phosphate salt.

As iron salt, mention may in particular be made of iron citrate or, particularly advantageously, iron chloride.

As phosphate salt, use may in particular be made of sodium phosphate.

The iron phosphate can be prepared by simultaneously or successively mixing the two starting components. The order of the mixing can be either the addition of iron chloride to sodium phosphate or, conversely, the addition of sodium phosphate to iron chloride. The rate of addition can be very rapid or, on the contrary, dropwise.

To obtain an iron phosphate suitable for the needs of the invention, it has been noted that a ratio of 2 times more iron salt than phosphate salt is satisfactory.

Alternatively, the iron phosphate can be prepared using a nebulizer. In this case, the sodium phosphate can be nebulized in a solution of iron chloride or, conversely, the iron chloride in the sodium phosphate.

During the preparation of the vaccine compositions according to the invention, the iron phosphate can be introduced into the vaccine composition at the very beginning of the formulation. The iron phosphate is then diluted to a certain concentration, and the antigens of interest are then added thereto.

Alternatively, it is possible to add the iron phosphate to a lyophilisate already comprising the portion of the vaccine composition which contains the antigens of interest.

According to the invention, the iron phosphate is present in the vaccine composition in a sufficient amount to exert an adjuvant action.

When it is the only adjuvant used, the dose of vaccine composition administered can comprise between 0.2 and 1.4 mg of iron phosphate.

When it is combined with another adjuvant, the amounts present can be reduced, as a function of the desired adjuvant effect and of the potency of the other adjuvants present.

Local and systemic toxicity tests on rabbits have shown that iron phosphate is as well tolerated as aluminum hydroxide.

The following examples illustrate particular embodiments of the present invention.

EXAMPLE 1

Preparation of Iron Phosphate and of Iron Hydroxide

The iron phosphate is prepared by mixing $FeCl_3.6H_2O$ at 0.5 M (supplied by SIGMA under the batch reference 55H 1251) in a solution of $Na_2HPO_4.2H_2O$ at 0.25 M (supplied by Merck with the batch reference FA004911). The 2 products are mixed in the following proportions: 1 l of ultrafiltered water comprising 44.5 g of $Na_2HPO_4.2H_2O$ is combined with a solution of 800 ml of ultrafiltered $H_2O$ comprising 108.12 g of $FeCl_3.6H_2O$. The mixing is performed at ambient temperature.

Stirring is performed for 15 minutes by means of a rod-stirrer and then successive centrifugations are carried out with the precipitate being washed with water. After each wash, the presence of chloride ions is detected by assaying the chloride ions with silver nitrate. When there are no longer any chloride ions, i.e. after 10 washes, the precipitate is taken up in water and autoclaved for 1 h at 118° C. in order to ensure its sterility.

The solution obtained in this manner is an iron phosphate solution containing 16 g Fe/l.

The iron hydroxide is prepared by mixing 0.5 M iron citrate and 2 M NaOH, at ambient temperature. NaOH is added dropwise to 100 ml of iron citrate until a pH of 8 is obtained. In the same way as for the preparation of the iron phosphate, stirring is performed for 15 minutes and then successive centrifugations are carried out with the precipitate being washed with water, and the chloride ions being assayed with silver nitrate. When chloride ions are no longer detected, the precipitate is taken up in water and autoclaved for 1 h at 118° C. in order to be sterile. The solution then obtained is an iron hydroxide solution containing 6.3 g Fe/l.

EXAMPLE 2

Preparation of the Vaccine Compositions

Using the solutions prepared as indicated above, an aqueous suspension of aluminum hydroxide (supplied by Reheis) comprising 10.8 g of Al/l, and also a preparation of PTP (purified tetanus protein) at a concentration of 330 flocculation or Lf units/ml (i.e. a protein concentration of 0.9125 g/l), the following compositions are prepared:

PTP alone: 840 µl $H_2O$+120 µl 9% NaCl+240 PTP at 100 Lf/ml,

PTP and AlOOH: 618 µl $H_2O$+222 µl AlOOH at 10.8 g of Al/l+120 µl 9% NaCl+240 PTP at 100 Lf/ml, PTP and $FePO_4$: 690 µl $H_2O$+150 µl $FePO_4$ at 16 g/l+120 µl of a 10 times-concentrated PBS buffer solution (i.e. 95 mM $Na_2HPO_4.2H_2O$)+240 PTP at 100 Lf/ml, PTP and FeOOH: 458 µl $H_2O$+382 µl FeOOH at 6.3 g of Fe/l+120 µl of a 10 times-concentrated PBS buffer solution+240 PTP at 100 Lf/ml.

EXAMPLE 3

Assaying of the Anti-Tetanus Antibodies 4 groups of six 6-week-old female OF1 mice are used.

One of the formulations prepared in example 2 is administered to each group of mice. The administration is performed intramuscularly in the quadriceps under anesthesia, at a rate of 2 injections of 50 µl on days D1 and D22. The amount administered is therefore 2 flocculation or Lf units of PTP and 0.2 mg of mineral material (either aluminum or iron) in the case of the formulations comprising an adjuvant.

On D15, a blood sample of approximately 300 µl is taken from the retro-orbital sinus in each mouse.

On D36, the mice are bled out under anesthesia, by sectioning of the carotid.

The PTP-specific IgG1s and IgG2as are assayed, by the ELISA method, on each of the sera corresponding to the bloods collected.

Figures 3, 4:
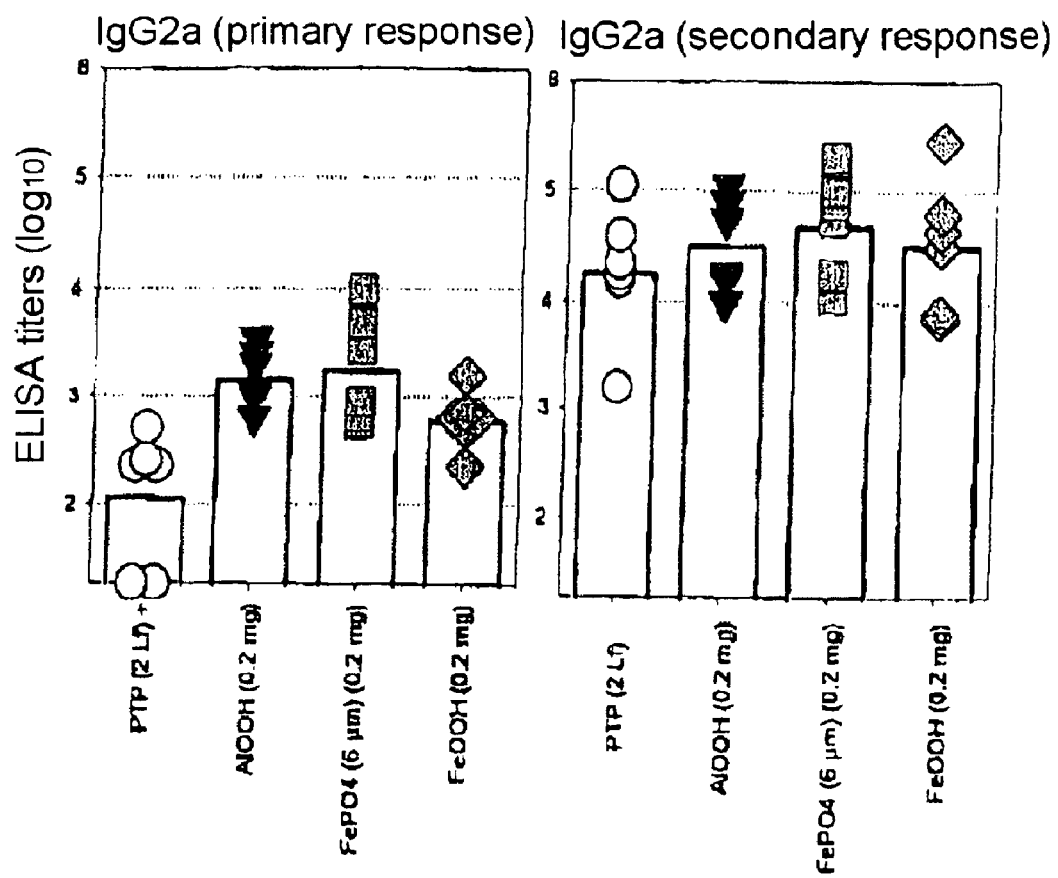

The results obtained are given in FIGS. 1 to 4 and show that the iron phosphate is a good adjuvant; as regards the IgG1s, the results obtained are clearly superior to those obtained when the antigen is administered alone, even though they are not quite as good as those obtained with the aluminum hydroxide; as regards the IgG2as, the titers obtained are as high as those obtained with the aluminum hydroxide.

EXAMPLE 4

Verification of the Anti-Tetanus Activity

The anti-tetanus activity of the compositions according to the invention is verified by means of a test consisting in evaluating, in mice, the activity of these compounds with respect to a lethal dose of toxin administered subcutaneously.

The activity of the compositions tested is determined by comparing the dose required to protect 50% of the animals ($ED_{50}$) against the effects of the toxin, with that of a reference vaccine calibrated in IU/ml.

The formulations tested are obtained by mixing the adjuvant (0.6 mg/dose) with water, 30 Lf of PDT (diphtheria toxoid) and 10 Lf of PTT (tetanus toxoid), and then adding 20 µg/dose of merthiolate and a saline solution (solution containing 90 g/l of NaCl and 5 mM $Na_2HPO_4.2H_2O$).

The vaccine compositions tested comprise either aluminum hydroxide or iron phosphate or iron hydroxide.

The results obtained with each of the adjuvants tested are reported in the table below, and show that iron phosphate is a good adjuvant, clearly better than iron hydroxide under the same conditions:

| Adjuvants | Tetanus activity (IU/dose) |
| --- | --- |
| AlOOH | 103 (76–139) |
| $FePO_4$ | 32 (24–43) |
| FeOOH | 8.2 (5.4–12.5) |

I claim:

1. A composition comprising at least one vaccine antigen and at least one adjuvant, wherein the adjuvant comprises iron phosphate.

2. The composition according to claim 1, wherein the iron phosphate is present in the form of a suspension of particles, the size of which is between 0.01 μm and 300 μm.

3. The composition according to claim 2, wherein the size of the particles is between 1 and 40 μm.

4. The composition according to claim 2, wherein the size of the particles is centered around a value of 7 μm.

5. The composition according to claim 1, wherein the iron phosphate is prepared from a solution of iron salt and of phosphate salt.

6. The composition according to claim 1, which comprises at least the tetanus antigen.

7. The composition according to claim 1, which comprises at least the diphtheria antigen.

8. The composition according to claim 1, which comprises at least one poliomyelitis antigen.

* * * * *